United States Patent
Belliere-Baca et al.

(10) Patent No.: US 12,351,549 B2
(45) Date of Patent: Jul. 8, 2025

(54) AGENT FOR INITIATING A RADICAL ADDITION REACTION AND PROCESS USING IT

(71) Applicant: ADISSEO FRANCE S.A.S., Antony (FR)

(72) Inventors: Virginie Belliere-Baca, Millery (FR); Olivier Peruch, Lyons (FR); Didier Morvan, Mornant (FR); Antoine Petrelli, Lyons (FR)

(73) Assignee: ADISSEO FRANCE S.A.S., Antony (FR)

( * ) Notice: Subject to any disclaimer, the term of this patent is extended or adjusted under 35 U.S.C. 154(b) by 855 days.

(21) Appl. No.: 17/423,273

(22) PCT Filed: Jan. 16, 2020

(86) PCT No.: PCT/FR2020/050059
§ 371 (c)(1),
(2) Date: Jul. 15, 2021

(87) PCT Pub. No.: WO2020/148509
PCT Pub. Date: Jul. 23, 2020

(65) Prior Publication Data
US 2022/0127223 A1    Apr. 28, 2022

(30) Foreign Application Priority Data

Jan. 18, 2019   (FR) ..................................... 19/00461

(51) Int. Cl.
*C07C 323/52* (2006.01)
*C07C 319/18* (2006.01)
*C07C 323/12* (2006.01)

(52) U.S. Cl.
CPC .......... *C07C 323/52* (2013.01); *C07C 319/18* (2013.01); *C07C 323/12* (2013.01)

(58) Field of Classification Search
None
See application file for complete search history.

(56) References Cited

U.S. PATENT DOCUMENTS 5,973,200 A * 10/1999 Koenig ................. C07C 319/18
562/556
8,153,846 B2    4/2012 Herzog et al.

FOREIGN PATENT DOCUMENTS

| EP | 1153936 A2 | 11/2001 |
|---|---|---|
| JP | H08119932 A | 5/1996 |
| WO | 8606729 A1 | 11/1986 |
| WO | 9832735 A1 | 7/1998 |
| WO | 2017191196 A1 | 11/2017 |

OTHER PUBLICATIONS

National Center for Biotechnology Information (2024). PubChem Compound Summary for CID 878, Methanethiol. Retrieved May 15, 2024 from https://pubchem.ncbi.nlm.nih.gov/compound/Methanethiol (Year: 2024).*
National Center for Biotechnology Information (2024). PubChem Compound Summary for CID 545123, Methyl 2-hydroxybut-3-enoate. Retrieved May 15, 2024 from https://pubchem.ncbi.nlm.nih.gov/compound/Methyl-2-hydroxybut-3-enoate (Year: 2024).*
Eun-Tae Yun et al, "Exploring the Role of Persulfate in the Activation Process: Radical Precursor Versus Electron Acceptor", Environmental Science & Technology, Sep. 5, 2017, vol. 51, No. 17, pp. 10090-10099, XP055640934.
International Search Report issued Jun. 3, 2020 re: Application No. PCT/FR2020/050059, pp. 1-3, Lenka et al. "Polymerization of acrylonitrile . . . ", Samal et al. "Acidic Peroxo Salts . . . ", Eun-Tae et al. "Exploring the Role of Persulfate . . . ", WO 9832735 A1 and U.S. Pat. No. 8,153,846 B2.
Rajani K Samal et al, "Acidic peroxo salts: a new class of initiators for vinyl polymerization. IV. Kinetics of polymerization of methyl methacrylate initiated by potassium monopersulfate catalyzed by silver(I)", Jan. 1, 1983, vol. A19, No. 4, p. 475-486, P009517117.
Subasini Lenka et al., "Polymerization of acrylonitrile initiated by potassium persulfate-cobalt(II) and potassium persulfate-manganese(II) redox systems", Aug. 1, 1983, vol. A20, No. 3, p. 397-407, XP009517116.

* cited by examiner

*Primary Examiner* — Amy C Bonaparte
(74) *Attorney, Agent, or Firm* — CANTOR COLBURN LLP

(57) ABSTRACT

An agent for initiating a radical addition reaction includes a persulfate and one or more transition metals, in elemental form or in an oxidized form, as well as a method for preparing a compound of formula (I)

[Chem I]

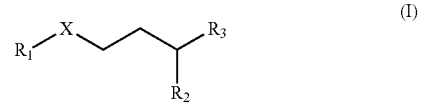

in which
  X is selected from S, Se and O;
  by a radical addition reaction in the presence of such an agent.

6 Claims, No Drawings

AGENT FOR INITIATING A RADICAL ADDITION REACTION AND PROCESS USING IT

TECHNICAL FIELD

The disclosure concerns an agent for the initiation of a radical addition reaction and its application in a method for preparing a compound of formula

[Chem I]

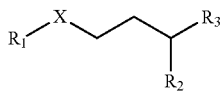

in which

X is selected from S, Se and O;

$R_1$ is selected from H, alkyl groups, aryl groups and alkylaryl groups;

$R_2$ is selected from H; OH; $NR_4R_5$, $NHCOR_4$; $OCOR_4$; where $R_4$ and $R_5$ are the same or different and are selected from H, alkyl groups, aryl groups, alkylaryl groups; and protecting groups;

$R_3$ is selected from OH, $CH_2OH$, COOH, COORS where $R_6$ is selected from alkyl, CN, $CONR_4R_5$ where $R_4$ and $R_5$ are as defined above, and COZ where Z represents a halide;

by a radical addition reaction in the presence of such an agent.

BACKGROUND

According to WO98/32735A1, there is known a method for preparing methionine and hydroxymethylthiobutyric acid (HMTBA), as well as their derivatives, by radical addition of methylthiol to a compound of the formula below

[Chem I]

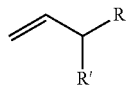

in which R is selected from COOH and the corresponding ester, amide, nitrile and trichloro functions and R' is selected from OH, $NH_2$, oxycarbonyl and aminocarbonyl functions and protecting groups. This reaction is initiated in the presence of an initiator agent consisting of azobisisobutyronitrile (AIBN) at a temperature in the range of 50° C. to 60° C. under a pressure in the range of 3.5 bars to 4.8 bars, or by UV irradiation. It leads to yields of at least 80%. The proven lessons of this document, and in particular regarding the above conditions, are limited to obtaining the HMTBA. The use of AIBN or its derivatives in this reaction has several drawbacks: the reaction time is long and thermal activation is required with a temperature which is generally above 50° C. In addition, the regioselectivity of the addition is low and purification by distillation of the fractions is more often necessary. Finally, such initiator agents are expensive, unstable and difficult to handle, which leads to safety problems during their transport, storage and handling, as well as to costs.

Document WO2017/191196A1 describes a method for manufacturing methionine by the same radical addition reaction as WO98/32735A1, by reaction of methylthiol with vinylglycine in the presence of an initiation agent selected from AIBN, N-bromosuccinimide (NBS), benzoyl peroxide (DBPO) and 2,2'-azobis[2-(2-imidazolin-2-yl)propane]hydrochloride or by UV irradiation optionally in the presence of a photoinitiation agent. The yields are very variable depending on the operating conditions. The authors had also illustrated this reaction in the presence of ammonium persulfate, but it only led to a conversion rate of vinylglycine to methionine of 23%, demonstrating the ineffectiveness of such an agent in this indication.

Thus, we are still looking for alternative solutions for the efficient synthesis of compounds by selective radical addition, using energy-free and easily industrializable conditions.

SUMMARY

According to the disclosure, an agent has been discovered for the initiation of a radical addition reaction making it possible to solve the problems of the known methods, in particular in a method of the disclosure as defined above.

This agent comprises or consists of a persulfate and one or more transition metals, the latter(s) being present in elemental form or in oxidized form.

Unexpectedly, said transition metal behaves as a powerful co-initiator of a persulfate in a radical addition reaction, in a temperature range close to room temperature. This discovery allows solving the selectivity problem associated with the use of persulfate which, to be active, must occur in a heated reaction medium, such conditions resulting in an inevitable loss of selectivity.

According to the disclosure, the persulfates can be replaced in some cases by organic peroxides depending on the objective and the constraints on the quality of the reaction product and the method effluents.

This initiator agent and its advantages are in the remainder of the text more specifically described in the context of a radical addition reaction of a thiol, a disulfide, a selenol, a diselenide or an alcohol on a vinyl compound such as a compound of formula (III) shown below. It is of course not restricted thereto, and the disclosure relates to such an agent which can be used for any radical addition reaction of a thiol, a disulfide, a selenol, a diselenide or an alcohol, on a compound carrying a double bond which is unconjugated, and which is terminal or not. This agent is particularly advantageous when a high selectivity is expected.

It is known that sodium persulfate is used, because of its strong oxidizing power and its stability, for soil remediation. In this mechanism, persulfate breaks down pollutants into harmless small molecules like $CO_2$, water and sulfates. In this application, it is used in the form of aqueous solutions at a concentration of approximately 5% and rapidly generates radicals after activation, some of which have a powerful oxidizing power. It acts on several types of polluting compounds, mainly hydrocarbons, the degradation of which generates various small-sized products.

The discovery according to the disclosure of the use of a persulfate in combination with a transition metal as an initiator of a selective radical reaction is therefore surprising. The characteristics, applications and advantages of the disclosure are set out below in more detail, given that these characteristics can be considered independently of one another, or in combination, whatever the combination.

Before this description, certain used terms are defined below.

The term «persulfate» means the oxyanion $S_2O_8^{2-}$, or its salt formed with any counterion.

The term «organic peroxide» means any organic species of formula $R_7$—O—O—$R_8$ with $R_7$ and $R_8$, identical or different, being selected from H, alkyl groups, aryl groups, alkylaryl groups and CO—$R_1$ groups where $R_1$ is as defined below.

A radical addition reaction responds to a chain reaction mechanism comprising an initiation which takes place from an initiation agent, a propagation which sees the radical(s) formed during the initiation react with a compound and then the termination.

The term «elemental form of a metal» means a metal in oxidation state 0, or otherwise expressed, a metal in its reduced form.

The term «oxidized form of a metal» includes any association of a metal with an anion(s) or with oxygen, at any degree of oxidation of the metal. This definition includes oxides, sulfates, phosphates, chlorides (for example $FeCl_3$), carbonates, hydroxides, nitrites, nitrates, acetates, alcoholates, hydrogen phosphates and hydrogen sulfates.

In the formulas defining the compounds obtained or used, the term «alkyl» denotes a linear or branched monovalent hydrocarbon radical having from 1 to 20 carbon atoms, advantageously from 1 to 6 carbon atoms, such as methyl or ethyl, propyl, isopropyl, butyl, isobutyl, tert-butyl, pentyl, neopentyl, n-hexyl or a cyclic monovalent hydrocarbon radical having from 3 to 20 carbon atoms, advantageously from 3 to 6 carbon atoms, such as cyclopropyl, cyclohexyl.

The term «aryl group» is understood to mean an aromatic monovalent hydrocarbon radical comprising from 6 to 22 carbon atoms.

The term «alkylaryl group» means an aryl group comprising from 6 to 22 carbon atoms, said aryl group being substituted by at least one alkyl group corresponding to the definition above.

DETAILED DESCRIPTION OF THE DISCLOSURE

Thus the disclosure concerns the application of an agent for the initiation, or initiator agent, or primer agent, in a radical addition reaction, said agent comprising or consisting of a persulfate and one or more transition metals, under elemental form or in an oxidized form.

The persulfate can be in the form of a salt of a cation, the associated cation preferably being selected from sodium, potassium, calcium, lithium and ammonium ions, although any counterion may be suitable.

As indicated above, according to the disclosure, the persulfates can be, in certain cases, advantageously replaced by organic peroxides.

The persulfate can be combined with one or more transition metals. When several metals are used, the mixtures may consist of the same metal in the elemental state and/or in different degrees of oxidation; different metals in elemental state and/or in the same degree of oxidation or in different degrees of oxidation, but also in the form of alloys such as for example brass, possibly in oxidized form.

The transition metal(s) are advantageously selected from Cu, Zn and Fe, in their elemental form or in an oxidized form as defined above.

Advantageously, the molar ratio of persulfate to the transition metal(s) ranges from 0.5 to 10,000. An excess of metal can lead to a drop in the selectivity of the reaction, but too low a content will slow down the reaction, affecting its industrializable interest. Preferably, this molar ratio ranges from 1 to 1000.

According to the disclosure, the aforementioned combination of a persulfate and one or more transition metals is applied to the initiation of a radical addition reaction involving an organic entity capable of forming a radical which reacts on a double bond. This double bond is unconjugated. It may or may not be terminal.

In the context of the disclosure, the initiator agent is used in very small proportions relative to the organic species involved in the reaction. Thus, the molar ratio of the organic species on which the initiator agent acts directly to said agent ranges from 2 to 1000. It is within the competence of one skilled in the art to adjust the value of this ratio as well as possible. The persulfate is preferably used in solution in an inert solvent. This can consist of water and any aqueous mixture containing a water soluble organic solvent such as an alcohol. According to a preferred variant of implementation of the initiator agent, the compound (III) is mixed with the metal, then the compound (II) is added, and finally the persulfate solution is slowly poured into this mixture.

The disclosure also concerns one of the applications of this initiator agent, and specifically its use for obtaining compounds of formula (I) cited above, namely,

[Chem I]

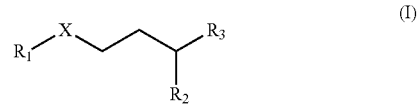

in which

X is selected from S, Se and O;

$R_1$ is selected from H, alkyl groups, aryl groups and alkylaryl groups;

$R_2$ is selected from H; OH; $NR_4R_5$; $NHCOR_4$, $OCOR_4$, where $R_4$ and $R_5$ are identical or different and are selected from H, alkyl groups, aryl groups, alkylaryl groups; and protecting groups;

$R_3$ is selected from OH, $CH_2OH$, COOH, $COOR_6$ where $R_6$ is selected from alkyl, CN, $CONR_4R_5$ where $R_4$ and $R_5$ are as defined above, and COZ where Z represents a halide;

said method comprising the reaction of a compound of formula (II)

[Chem II]

in which

X is selected from S, Se and O;

$R_1'$ is selected from H, alkyl, aryl, alkylaryl, thiol, thioalkyl, thioaryl, thioalkylaryl, selenol, selenoalkyl, selenoaryl and selenoalkylaryl groups, and $R_2'$ is selected from H, alkyl groups, aryl groups and alkylaryl groups;

with a compound of formula (III)

[Chem III]

(III)

where $R_2$ and $R_3$ are as defined above for the compound of formula (I).

The initiator agent as described above, that is to say responding to any one or several of the mentioned characteristics, is suitable for this reaction.

The work carried out on this reaction has, however, made it possible to determine the preferred variants indicated below, which can be considered alone or in combination, according to which the method is the most efficient, in particular is the most selective.

Thus, the persulfate is preferably potassium persulfate or sodium persulfate.

The molar ratio of compound (II) or of compound (III) to the initiator agent advantageously ranges from 2 to 1000, and better still from 10 to 500.

The molar ratio of compound (II) to compound (III) ranges from 0.9 to 20, preferably from 1.1 to 3.

As said before, the use of an initiator agent of the disclosure allows the reaction temperature to be lowered; that can be carried out at a temperature of −20° C. to 60° C., preferably from −20 to 40° C., or even from 0° C. to 40° C., and even from 10° C. to 40° C. Such conditions are favorable for high selectivity, without affecting the reaction yield.

The initiator agent of the disclosure can be implemented for the radical addition of a compound (II) selected from methylthiol and methylselenol and of a compound (III) as defined above. It can also be used for the radical addition of a compound of formula (II) as generally defined above and of methyl vinyl glycolate, as compound (III).

According to a variant of the disclosure, the method is aimed at the preparation of HMTBA or its selenium analogue, hydroxymethyl selenobutyric acid (HMSeBA), as compound (I). HMTBA and HMSeBA can be obtained by the radical addition of methylthiol or methyl selenol, respectively, as compound (II), to methyl vinyl glycolate as compound (III) followed by hydrolysis of the formed correspondent ester.

EXAMPLES

The disclosure and its advantages are illustrated in the examples below.

Example 1: Preparation of methyl 2-hydroxy-4-(methylthio) butanoate by Radical Addition Reaction with an Initiator Agent According to the Disclosure 26.0 g (0.22 mol) of methyl 2-hydroxybut-3-enoate and 0.17 g of metallic copper (0.00027 mol) are placed in a stirred reactor and cooled to −10° C. 12.1 g of methanethiol (0.25 mol) are then injected, then an aqueous solution of sodium persulfate (0.023 mol) is slowly added.

The temperature is increased to 0° C. and the mixture is left under stirring for one hour.

HPLC analysis of the mixture at the end of the reaction indicates an 81% yield of methyl 2-hydroxy-4-(methylthio) butanoate (selectivity of 81%).

Comparative Example 1: Preparation of methyl 2-hydroxy-4-(methylthio)butanoate by Radical Addition Reaction with a Persulfate Compound Alone at Elevated Temperature 40.1 g (0.34 mol) of methyl 2-hydroxybut-3-enoate are placed in a stirred reactor and cooled to −15° C. 18.0 g of methanethiol (0.37 mol) are then injected, then an aqueous solution of sodium persulfate (0.034 mol) is slowly added.

The temperature is increased to 60° C. and the mixture is left under stirring for two hours.

HPLC analysis of the mixture at the end of the reaction indicates a 7.6% yield of methyl 2-hydroxy-4-(methylthio) butanoate (15% selectivity).

Example 2: Preparation of methyl 4-(butylsulfanyl)-2-hydroxybutanoate by Radical Addition Reaction with an Initiator Agent According to the Disclosure 20.4 g (0.18 mol) of methyl 2-hydroxybut-3-enoate and 0.025 g of metallic copper (0.00040 mol) are placed in a stirred reactor and cooled to −10° C. 17.7 g of butanethiol (0.20 mol) are then injected, then an aqueous solution of sodium persulfate (0.0054 mol) is slowly added.

The temperature is increased to 25° C. and the mixture is left under stirring for one hour.

HPLC analysis of the mixture at the end of the reaction indicates a 16% yield of methyl 4-(butylsulfanyl)-2-hydroxybutanoate.

Example 3: Preparation of 3-(methylsulfanyl) propan-1-ol by Radical Addition Reaction with an Initiator Agent According to the Disclosure 14.8 g (0.25 mol) of propen-3-ol and 0.015 g of metallic copper (0.00023 mol) are placed in a stirred reactor and cooled to −10° C. 13.5 g of methanethiol (0.28 mol) are then injected, then an aqueous solution of sodium persulfate (0.0077 mol) is slowly added.

The temperature is increased to 0° C. and the mixture is left under stirring for one hour.

HPLC analysis of the mixture at the end of the reaction indicates a quantitative yield of 3-(methylsulfanyl) propan-1-ol.

Example 4: Preparation of methyl 2-hydroxy-4-(methylthio) butanoate by Radical Addition Reaction with an Initiator Agent According to the Disclosure 26.3 g (0.23 mol) of methyl 2-hydroxybut-3-enoate and 0.020 g of iron (II) and iron (III) oxide (0.00013 mol) are placed in a stirred reactor and cooled to −10° C. 13.2 g of methanethiol (0.27 mol) are then injected, then an aqueous solution of sodium persulfate (0.023 mol) is slowly added.

The temperature is increased to 0° C. and the mixture is left under stirring for one hour.

HPLC analysis of the mixture at the end of the reaction indicates a 79% yield of methyl 2-hydroxy-4-(methylthio) butanoate.

Example 5: Preparation of methyl 2-hydroxy-4-(methylthio) butanoate by Radical Addition Reaction with an Initiator Agent According to the Disclosure 26.1 g (0.22 mol) of methyl 2-hydroxybut-3-enoate and 0.089 g of iron sulfate (0.00022 mol) are placed in a stirred reactor and cooled to −10° C. 12.0 g of methanethiol (0.25 mol) are then injected, then an aqueous solution of sodium persulfate (0.023 mol) is slowly added.

The temperature is increased to 0° C. and the mixture is left under stirring for one hour.

HPLC analysis of the mixture at the end of the reaction indicates a 70% yield of methyl 2-hydroxy-4-(methylthio) butanoate (selectivity of 84%).

These examples demonstrate the performance of an initiator agent according to the disclosure and of a method implementing it.

The invention claimed is:

1. A method for preparing a compound of formula (I)

[Chem I]

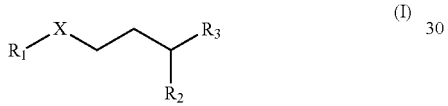
(I)

in which

X is selected from S and Se;

$R_1$ is selected from H and alkyl groups;

$R_2$ is selected from H; OH; $NR_4R_5$; $NHCOR_4$ and $OCOR_4$; where $R_4$ and $R_5$ are identical or different and are selected from H and alkyl groups;

$R_3$ is selected from OH; $CH_2OH$; COOH; $COOR_6$; CN; $CONR_4R_5$; and COZ, wherein $R_6$ is selected from alkyl, $R_4$ and $R_5$ are as defined above, and Z represents a halide;

the method comprising the reaction of a compound of formula (II)

[Chem II]

(II)

in which

X is selected from S and Se;

$R_1'$ is selected from:
  alkyl, groups;
  thiol and thioalkyl groups when X is S; and
  selenol and selenoalkyl groups when X is Se, and
$R_2'$ is selected from H and alkyl groups;
with a compound of formula (III)

[Chem III]

(III)

where $R_2$ and $R_3$ are as defined above for the compound of formula (I),
in the presence of at least one initiation agent for initiating a radical addition reaction comprising a persulfate and one or several transition metals, in elemental form or in oxidized form, said transition metal(s) being selected from Cu, Zn, Fe and their alloys in their elemental form or in an oxidized form selected from sulfates, phosphates, chlorides, carbonates, nitrites, nitrates, acetates, alcoholates, hydrogenphosphates, and hydrogen sulfates,
wherein the molar ratio of persulfate to the transition metal(s) ranges from 1:1 to 1000:1, and
wherein the reaction is carried out at a temperature from −20° C. to 40° C.

2. The method according to claim 1, wherein the persulfate is in the form of a salt of a cation.

3. The method according to claim 1, wherein the persulfate is potassium persulfate or sodium persulfate.

4. The method according to claim 1, wherein the molar ratio of compound (II) to compound (III) ranges from 1.1:1 to 3:1.

5. The method according to claim 1, wherein the compound (II) is methylthiol or methylselenol.

6. The method according to claim 1, wherein the compound (III) is methyl vinyl glycolate.

* * * * *